(12) United States Patent
Sannigrahi et al.

(10) Patent No.: US 8,497,097 B2
(45) Date of Patent: Jul. 30, 2013

(54) CHLORINE DIOXIDE TREATMENT OF BIOMASS FEEDSTOCK

(75) Inventors: Poulomi Sannigrahi, Atlanta, GA (US); Arthur J. Rasgauskas, Lawrenceville, GA (US); Stephen J. Miller, San Francisco, CA (US)

(73) Assignees: Georgia Tech Research Corporation, Atlanta, GA (US); Chevron U.S.A., Inc., San Ramon, CA (US)

( * ) Notice: Subject to any disclaimer, the term of this patent is extended or adjusted under 35 U.S.C. 154(b) by 80 days.

(21) Appl. No.: 12/854,758

(22) Filed: Aug. 11, 2010

(65) Prior Publication Data

US 2012/0040413 A1   Feb. 16, 2012

(51) Int. Cl.
   *C12P 19/02*   (2006.01)
(52) U.S. Cl.
   USPC ............................................. 435/105; 435/7.1
(58) Field of Classification Search
   None
   See application file for complete search history.

(56) References Cited

U.S. PATENT DOCUMENTS

| | | | | |
|---|---|---|---|---|
| 4,008,136 | A * | 2/1977 | Williams | 210/748.08 |
| 5,328,562 | A * | 7/1994 | Rafferty et al. | 162/21 |
| 5,762,808 | A * | 6/1998 | Peyton | 210/748.04 |
| 6,419,788 | B1 * | 7/2002 | Wingerson | 162/14 |
| 6,620,292 | B2 * | 9/2003 | Wingerson | 162/19 |
| 7,320,741 | B2 * | 1/2008 | Tolan et al. | 162/73 |
| 7,368,036 | B2 * | 5/2008 | Tolan et al. | 162/73 |
| 7,488,425 | B2 * | 2/2009 | Fuchigami et al. | 210/748.09 |
| 7,666,637 | B2 * | 2/2010 | Nguyen | 435/165 |
| 8,192,968 | B2 * | 6/2012 | Edwards et al. | 435/158 |
| 2005/0067122 | A1 * | 3/2005 | Kazem et al. | 162/29 |
| 2008/0032344 | A1 | 2/2008 | Fallavollita | |
| 2008/0057555 | A1 | 3/2008 | Nguyen | |
| 2009/0061490 | A1 * | 3/2009 | Edwards et al. | 435/105 |
| 2009/0229599 | A1 | 9/2009 | Zhang | |

FOREIGN PATENT DOCUMENTS

| | | |
|---|---|---|
| WO | WO 2009/060126 A1 | 5/2009 |
| WO | WO 2009/080737 A2 | 7/2009 |
| WO | WO 2009/092749 A1 | 7/2009 |

OTHER PUBLICATIONS

Phillips (National Renewable Energy Laboratory (NREL/TP 510-41168).*
Li (Sun Grant Initiative, pp. 1-40, 2005).*
International Search Report of corresponding counterpart international application No. PCT/US2011/047452 dated Dec. 22, 2011.
Pan et al., "Pretreatment of Lodgepole Pine Killed by Mountain Pine Beetle Using the Ethanol Organosoly Process . . . ", 46 Ind. Eng. Chem. Res. (2007), pp. 2609-2617.
Arato et al., "The Lignol Approach to Biorefining of Woody Biomass to Produce Ethanol and Chemicals", 121-124 Appl. Biochem. & Biotech (2005), pp. 871-882.
Botello et al., "Recovery of Solvent and By-Products from Organosolv Black Liquor", 34(12) Separation Sci. & Tech. (1999), pp. 2431-2445.
Larsson et al., "A CP/MAS 13C NMR investigation of molecular ordering in celluloses", 302 Carbohydrate Res. (1997), pp. 19-25.
Lennholm et al., "Determination of cellulose I-alpha and I-beta in lignocellulosic materials", 261 Carbohydrate Res. (1994), pp. 119-131.
Li et al., "Carbohydrate Reactions During High-Temperature Steam Treatment of Aspen Wood", 125 Appl. Biochem. & Biotech. (2005), pp. 175-188.
Martinez et al., "Use of UV Absorbance to Monitor Furans in Dilute Acid Hydrolysates of Biomass", 16 Biotechnol. Prog. (2000), pp. 637-641.
Pu et al., "CP/MAS 13C NMR analysis of cellulase treated bleached softwood kraft pulp", 341(5) Carbohydrate Res. (2006), pp. 591-597.
Li et al., "Lignin depolymerization / repolymerization and its critical role for delignification of aspen wood by steam explosion", 98 Biores. Technol. (2007), pp. 3061-3068.
Pan et al., "Bioconversion of Hybrid Poplar to Ethanol and Co-Products Using an Organosolv Fractionation Process . . . ", 94(5) Biotech. & Bioeng. (2006), pp. 851-861.

* cited by examiner

*Primary Examiner* — Hope Robinson

(57) ABSTRACT

The instant invention pertains to the use of chlorine dioxide in new processes for treating lignocellulosic feedstocks, as well as, new compositions suitable for, for example, bioalcohol production. Advantageously, the processes and compositions of the present invention may be used in more environmentally friendly, cost-efficient production of fuels and, if desired, may be coupled with other biomass processing facilities such as Kraft pulp bleaching mills.

20 Claims, 2 Drawing Sheets

CHLORINE DIOXIDE TREATMENT OF BIOMASS FEEDSTOCK

FIELD OF THE INVENTION

The instant invention pertains to the use of chlorine dioxide in new processes for treating lignocellulosic feedstocks, as well as, new compositions suitable for, for example, bioalcohol production.

BACKGROUND AND SUMMARY OF THE INVENTION

In light of energy demand and environmental concerns, processes and compositions for the production of fuels from renewable feedstocks are needed. A common process involves producing ethanol from corn. Unfortunately, using corn and the like as precursors competes with food and feed supplies. Accordingly, other routes are being explored.

One such other route involves acid/enzymatic hydrolysis of, for example, lignocellulosic biomass feedstock followed by, for example, fermentation to produce bioalcohols such as ethanol. Unfortunately, many of these prior art approaches involve the use of or the producing a by-product of, for example, substances which may inhibit or poison heterogeneous catalysts such as noble metal catalysts that are sometimes used in downstream processing. Such substances include, for example, hydrogen sulfide, organic sulfur compounds, and/or halide ions. In some cases, the prior art approaches use, for example, mineral acids like sulfuric acid for acid hydrolysis of biomass. Unfortunately, these too may result in residual inorganic salt species and the like which can possibly affect the performance of downstream heterogeneous or enzyme catalysts. What's more, mineral acids may also be corrosive to conventional process equipment, may require the use of expensive alloys, and are generally not considered to be environmentally-friendly or green reagents. Unfortunately, other recent approaches such as those described in, for example, Pan et al., Ind. Chem. Res. 2007, 46, 2609-17; WO 2009/060126; WO 2009/080737; and 2009/092749 have other one or more other potential disadvantages such as requiring concentrated acids or mixtures of acids, low yields, degradation of desirable products such as soluble monosaccharides, and/or complex processing conditions.

Another prior art method that has been employed is described by Nguyen in U.S. Patent Application No. 2008/0057555. Nguyen soaks wood chips in acid and subjects them to increased pressure and temperature. The solids and liquids are separated from each other and hemicelluloses of the liquid stream are isolated for fermentation to ethanol. The solid lignin is packed in a 2-4 stage continuous, co-current reactor wherein each stage contains 1-10% solutions of sodium chlorite/anhydrous acetic acid (5:1); chlorine/chlorine dioxide (70:30); sodium hypochlorite or diluted hydrogen peroxide. The reactor temperature is maintained at 120-180 F for 1-3 hours. Once washed the cellulosic product can be subjected to simultaneous saccharification and fermentation or separate enzymatic hydrolysis followed by fermentation. Unfortunately, the method requires complex and specialized equipment and chemicals with long processing times. Additionally, such a specialized, complex process is not easily coupled with other processes employing such wood chip starting materials which would render the process less costly in regard to recycle and the like.

Accordingly, it would be desirable to discover new processes and compositions that could be employed in, for example, the production of fuels from renewable feedstocks. It would be advantageous if such processes and compositions did not require substances which may substantially inhibit or otherwise affect the performance of downstream heterogeneous or enzyme catalysts. It would further be advantageous if the substances employed were less corrosive, more environmentally-friendly, more dilute, and/or produced high yields without degrading desirable products and without the use of complex processing conditions. It would further be desirable if such a process could be coupled with other renewable feedstock processing facilities such as, for example, Kraft pulp bleaching mills and the like.

Fortunately, the present inventors have discovered new processes and compositions which may meet one or more of the aforementioned needs or even have other advantages. In one embodiment, the invention relates to a process for treating a lignocellulosic feedstock. The process comprises first contacting the feedstock with a solution comprising chlorine dioxide, ethanol, and water to form a mixture. Next, the mixture is heated at a temperature and time sufficient to produce a composition mixture comprising (1) a first solid portion comprising cellulose which is suitable for enzymatic hydrolysis, (2) a second solid portion comprising lignin or a derivative thereof, and (3) a solution comprising one or more hemicellulosic sugars.

In another embodiment, the invention relates to a composition comprising lignocellulosic feedstock and a solution comprising chlorine dioxide, ethanol, and water. The composition is characterized by (1) a ratio of feedstock to solution comprising chlorine dioxide and water of from about 1:3 to about 1:10; and (2) an amount of chlorine dioxide of from about 0.5% to about 5% by weight based on the total dry weight of dry feedstock.

In another embodiment, the invention relates to a process for treating a lignocellulosic feedstock. The process comprises first contacting the feedstock with a solution comprising chlorine dioxide, ethanol, and water to form a mixture, wherein the ratio of feedstock to solution comprising chlorine dioxide, ethanol, and water is from about 1:3 to about 1:10, wherein the amount of ethanol is from about 40 to about 80 weight percent based on the total amount of ethanol and water, and wherein the amount of chlorine dioxide is from about 0.5% to about 8% by weight based on the total dry weight of feedstock. Next, the mixture is heated at a temperature of at least about 180° C. for at least about 5 minutes to produce a composition mixture comprising (1) a first solid portion comprising cellulose which is suitable for enzymatic hydrolysis, (2) a second solid portion comprising lignin or a derivative thereof, and (3) a solution comprising hemicellulose. The second solid portion comprising lignin or a derivative thereof is separated from the solid first portion and at least part of the solid first portion is enzymatically hydrolyzed to form a composition comprising glucose. The glucose may be fermented to, for example, ethanol.

DETAILED DESCRIPTION OF THE INVENTION

Figure 1:
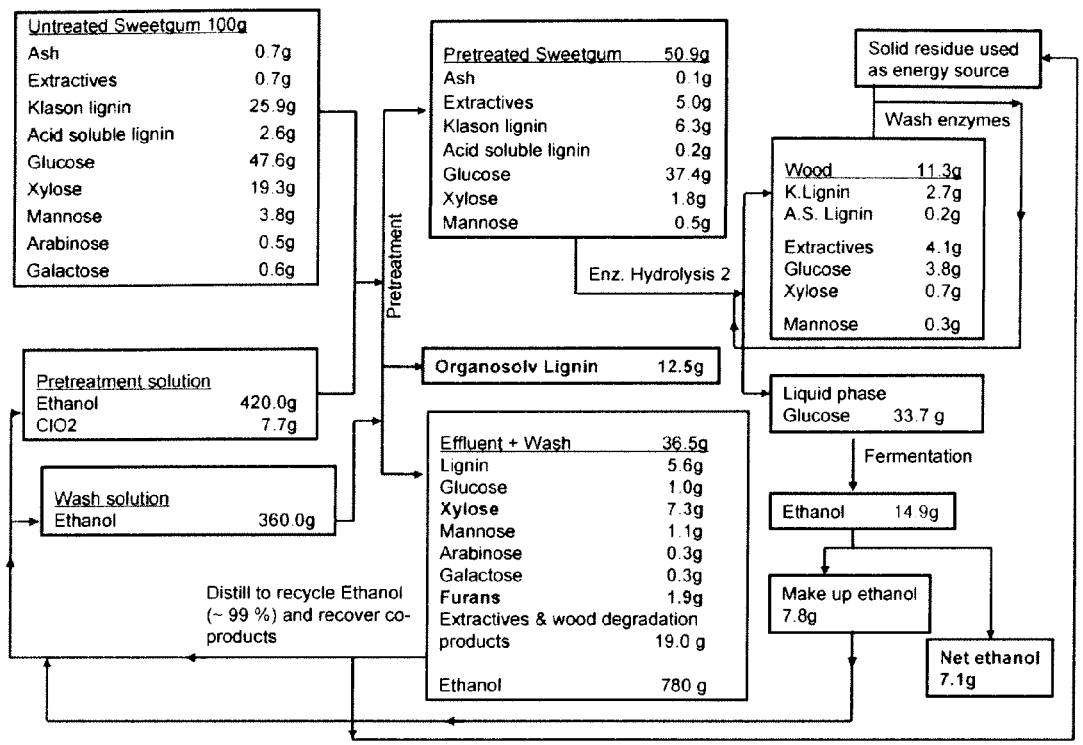
FIG. 1 shows a mass balance for example 1.

The instant invention pertains to the use of chlorine dioxide in new processes for treating lignocellulosic feedstocks, as well as, new compositions suitable for, for example, bioalcohol production.

As used herein, "cellulose" is a linear, unbranched polysaccharide with the formula $(C_6H_{10}O_5)n$ wherein n may be from several hundred to over 10,000.

As used herein, "hemicellulose" is a branched polysaccharide which is comprised of from several hundred to about 3000 sugar monomer units. The sugar monomers may include D-pentose sugars and smaller amounts of L-sugars. Such sugar monomers include, for example, xylose, mannose, galactose, rhammose, and arabinose. Hemicellulose is generally more complex than sugar but less complex than cellulose.

As used herein, "lignin" is a complex, non carbohydrate polymer generally found in wood which is capable of binding to cellulose fibers to strengthen the cell walls of plants. Lignin may be characterized as, for example, acid-soluble lignin or Klason lignin both as determined by NREL/TP 510-42618.

Feedstock

The nature of the feedstock employed in the processes and compositions herein is not particularly critical so long as the feedstock comprises holocellulose. As used herein, "holocellulose" means the water-insoluble carbohydrate portion of a biomass, i.e., the portion of the biomass that is not lignin, extractives, or ash, but rather, includes substances such as polysaccharides. The precise composition of holocellulose may vary depending upon the specific feedstock employed. However, holocellulose useful herein typically comprises various amounts of celluloses such as alpha-cellulose and hemicellulose and may contain various pentosan or hexosan polymers as measured by NREL/TP 510-42618. Thus, virtually any lignocellulosic biomass may be employed as the feedstock in the processes and compositions of the instant invention.

In one embodiment a particularly preferable feedstock is a plant biomass. Biomass comes in many different types, which may be grouped into a few main categories: wood or forestry residues, including sawmill and paper mill discards, municipal paper waste, algae, agricultural residues, including corn stover (stalks and straw), and sugarcane bagasse, and dedicated energy crops, which are mostly composed of fast growing tall, woody grasses such as, for example, switchgrass. Any of the aforementioned may find use in the instant invention. A particularly preferable biomass comprises one with high holocellulose content, i.e., hollocellulose content of greater than about 50, preferably greater than about 70 weight percent of the biomass as measured by NREL/TP 510-42618.

Depending upon the nature of the feedstock it may be desirable to reduce at least a portion of it in size in order to expose additional surface area for treatment. Such reduction may be done in any convenient manner such as by grinding, cutting, chopping, etc. The desired size of the feedstock varies depending upon the type of ingredients, equipment and other specifics of the instant inventions. Typically, smaller size feedstocks may react quicker but cost more to produce. Generally, it is advantageous if the feedstock is reduced prior to hydrolyzing to a particle size of less than about 25 mm, preferably less than about 10 mm, preferably less than about 8 mm, in its smallest dimension.

Similarly, it is often advantageous, or may even be necessary, in some situations to first purify at least a portion of the feedstock. By purify is meant to partially clean in order to remove at least some contaminants that may negatively effect downstream processes. This purification may assist in reducing or eliminating any undesired reactions in the following steps. The type of purification will depend upon the source of the feedstock, as well as, the amount and nature of the impurities and the following steps to which it will be subjected. Often, simple washing of the lignocellulosic feedstock is sufficient. Such purification, if done, may be accomplished prior to, in conjunction with, or subsequent to any size reduction. Additionally, if desired or advantageous, at least a portion or all of the feedstock that does not comprise hollocellulose may be separated. However, this is unnecessary for many processes and conditions to which the composition will likely be subjected.

Step (a)—Contacting Feedstock with Chlorine Dioxide, Ethanol, and Water Solution Initially, the feedstock is contacted with a solution comprising chlorine dioxide, ethanol, and water to form a mixture. The amounts of chlorine dioxide, ethanol, and water may vary depending upon the feedstock employed, the reaction conditions, and the desired results. Generally, the amounts of each ingredient and conditions of contact are such that the pH is usually reduced, and preferably reduced by at least about 1 unit, prior to the next step.

The amount of chlorine dioxide employed is at least about 0.5% in some embodiments. In other embodiments, the amount of chlorine dioxide employed is usually less than to about 8%, or sometimes even less than about 5% by weight based on the total dry weight of feedstock employed. The amount of ethanol varies but is generally at least about 40, or even at least about 50 percent by weight based on the total amount of ethanol and water. On the other hand, the amount of ethanol is generally less than about 80, or even less than about 70 percent by weight based on the total amount of ethanol and water. While not wishing to be bound to any particular theory it is believed that the ethanol assists in solubilization and leads to a potentially higher yield.

The ratio of feedstock to solution comprising chlorine dioxide, ethanol, and water is not particularly critical and may vary. In one embodiment a useful ratio of feedstock to solution comprising chlorine dioxide, ethanol, and water is from about 1:3 to about 1:10. In another embodiment a useful ratio of feedstock to solution is from about 1:3 to about 1:8.

The mixing of the aforementioned ingredients results in a composition comprising a lignocellulosic feedstock and a solution comprising chlorine dioxide, ethanol, and water. The composition is characterized by (1) a ratio of feedstock to solution comprising chlorine dioxide and water of from about 1:3 to about 1:10; and (2) an amount of chlorine dioxide of from about 0.5%, or about 0.8% to about 1.5%, or about 5%, by weight based on the total dry weight of dry feedstock. The ethanol may comprises from about 50, or about 60, to about 70, or 80, percent by weight based on the total amount of ethanol and water.

The initial contacting of the feedstock with the solution comprising chlorine dioxide, ethanol, and water is typically conducted in the presence of heat. That is, it is usually preferable to subject the mixture to mild heat. While not wishing to be bound to any particular theory it is believed that this initial mild heat treatment may assist in at least partially oxidizing at least some lignin and producing acidity in-situ. In this manner, the pH drops after the chlorine dioxide treatment in step (a).

The specific conditions of this mild heat treatment vary depending upon the feedstock, amounts of other ingredients, and desired results. Generally, the temperature is at least about 50° C. or at least about 60° C. in some embodiments. On the other hand, the temperature is usually less than about 90° C. or less than about 80° C. in some embodiments. The amount of time may vary as well. Normally, the heating in step (a) is conducted for a time of at least about 1 hour, or at least about 2 hours, or at least about 2.5 hours in some embodiments. Specifically, in various embodiments the feedstock is contacted with the solution comprising chlorine dioxide, ethanol, and water at a temperature of from about 50° C. to about 90° C. for a time of at least about 1 hour; or at a temperature of from about 60° C. to about 80° C. for a time of at least about 2 hours; or at a temperature of from about 60° C. to about 80° C. for a time of at least about 2.5 to about 3.5 hours.

Step (b)—Heating the Mixture at a Temperature and Time Sufficient to Produce a Composition Mixture Following step (a), the mixture is heated at a temperature and for a time sufficient to produce a composition mixture comprising (1) a first solid portion comprising cellulose which is suitable for enzymatic hydrolysis, (2) a second solid portion comprising lignin or a derivative thereof, and (3) a solution comprising hemicellulose.

The temperature of step (b) is generally higher and for a shorter period of time than in step (a). That is, the mixture in step (b) is usually heated at a temperature of at least about 180° C., or at least about 180° C. up to about 210° C. The heating time is advantageously kept as short as possible to produce the desired composition mixture. Generally, such times are at least about 5 minutes and in some embodiments at least about 30 minutes.

Once formed, the various portions may be separated and used as desired. Advantageously, the solid portions may be separated by precipitating the second solid portion comprising lignin or a derivative thereof and recovering the lignin by filtration. At least part of the first solid portion comprising cellulose may then be enzymatically hydrolyzed to form a composition comprising glucose which then may be fermented.

Although only exemplary embodiments are specifically illustrated and described herein, it will be appreciated that many modifications and variations of the process and apparatus described herein are possible in light of the above teachings and within the purview of the appended claims without departing from the spirit and intended scope of the claimed subject matter.

EXAMPLE 1

Chlorine Dioxide/Ethanol Treatment of Sawdust 40 oven-dried grams of sweetgum sawdust was added to 280 ml of 60% ethanol solution with 1.1% chlorine dioxide added. This step was performed in sealed plastic pouches, at 75° C. for 3 hours with a wood to solution ratio of 1:7. Heating is believed to result in the oxidation of lignin and the generation of in-situ acidity as the pH of the solution dropped from 5 to 3 after the chlorine dioxide treatment.

The wood and liquor were transferred to a glass liner of a Parr high-pressure reactor and heated at 180° C. for 1 h. Following completion of the treatment, the effluent was condensed and collected. 190 ml effluent of pH 5 was obtained. The organosolv treated wood was washed three times with 200 ml of 60% ethanol solution at 60° C. and the washes were combined with the effluent collected previously. The wood was then washed three times with water at 60° C. and the washes discarded. The combined effluent and ethanol wash solution was mixed with three volumes of water (1650 ml) to precipitate the dissolved lignin. The lignin precipitate, which is designated as ethanol organosolv lignin (EOL), was collected on a filter paper and air-dried. The filtrate comprises a water-soluble fraction containing lignin, sugars and possible degradation products. A mass balance diagram for example 1 is presented in FIG. 1.

The mass balance diagram in FIG. 1 is based on the literature. According to literature (Botello et al., 1999; Arato et al., 2005), about 99% of the ethanol can be recovered by distillation from the combined effluent and wash solutions after precipitating the organosolv lignin. So 1% of the ethanol input (3.3 g) should be cycled back in to the process. Water may also be partially recycled (~30% according to Botello et al., 1999). Other products that may be recovered from this solution include furfural (furans) and xylose. There is likely some loss of sugars, lignin and extractive material during the pretreatment stage. In the instant process, this is about 19.0 g, which is in the effluent plus wash fraction. This fraction may comprise degraded sugars, lignin fragments and compounds such as acetic acid. Some studies include acetic acid as a by-product that can be recovered by distillation.

The ethanol yield is 89% of the theoretical ethanol yield, so the remaining glucose after fermentation (~3.9 g) can be added back to the fermentation stream. The solid residue remaining after enzyme hydrolysis may be washed to recycle and reuse the enzymes. The remaining material may be used as a source of energy by burning it. The solid residue left after distillation of the ethanol, water and volatile products can also be utilized as an energy source if desired. The chlorine dioxide reacts to form chlorate and chloride ions, a fraction of which may get incorporated in the degraded lignin while the rest may remain in solution. The products include 12.5 g Organosolv lignin, 7.3 g Xylose, 1.9 g Furans, and Net ethanol 7.1 g.

EXAMPLE 2

Chlorine Dioxide Treatment of Sawdust without Ethanol

This step was performed as in Example 1 except that ethanol was not employed. That is it was performed in sealed plastic pouches, at 75° C. for 3 hours with a wood to 1.1% chlorine dioxide solution ratio of 1:10. Heating is believed to result in the oxidation of lignin and the generation of in-situ acidity as the pH of the solution dropped from 3 to 1 after the chlorine dioxide treatment. It was found that at higher $ClO_2$ loadings, i.e., 2.17%; 4.4% and 6.5% per oven dried weight of wood, high mass loss often occurred.

Figure 2:
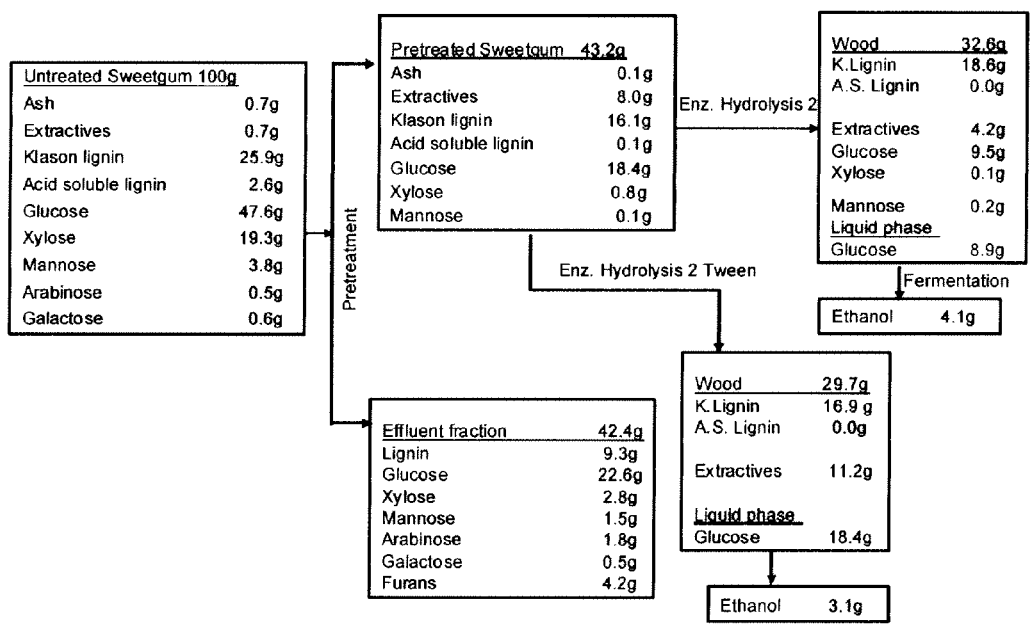
FIG. 2 shows a mass balance for example 2.

The wood and liquor were transferred to a glass liner of a Parr high-pressure reactor and heated at 204° C. for 10 minutes. The treated wood was washed with hot water and samples stored for characterization and enzyme hydrolysis. A mass balance diagram for example 2 is presented in FIG. 2.

EXAMPLE 3

Enzymatic Hydrolysis and Fermentation of Example 1

Enzyme hydrolysis of the cellulosic solid of Example 1 was performed using cellulase (Celluclast 1.5L) and β-glucosidase (Novozyme 188). Both enzymes were purchased from Sigma-Aldrich, St. Louis, MO. β-glucosidase or cellobiase was added to hydrolyze the cellobiose units, which are formed during cellulose hydrolysis by cellulase enzymes. This is useful since cellobiose may act as an inhibitor to cellulose hydrolysis. These low dose enzyme experiments were performed using 20 FPU cellulase and 40 IU β3-glucosidase per gram cellulose which is designated as "enzyme hydrolysis 1" in the mass balance diagrams of FIGS. 1 and 2.

The cellulosic solid of the pretreated wood of Example 1 (weight equivalent of 2 g cellulose) was suspended in 100 ml of pH 4.8, 50 mM acetate buffer solution containing the required amount of enzymes and hydrolyzed in a rotary shaker at 50° C. and 150 rpm. 1 ml aliquots of the solution were sampled periodically. The sample was placed in a boiling water bath for 10 minutes to deactivate the enzymes, centrifuged, and the supernatants stored frozen for glucose analysis. Glucose concentrations were quantified using HPLC and the percent cellulose to glucose conversion yield was calculated. Higher dose enzyme hydrolysis was performed with double the enzyme dose as described above. This condition is designated as "enzyme hydrolysis 2" in the mass balance diagrams of FIGS. 1 and 2.

The aqueous phase from enzymatic hydrolysis was fermented using Bakers' yeast (*Saccharomyces cerevisiae*). For these experiments, the solutions were filtered through a 0.45 µm membrane and their pH adjusted to ~5.5 by the drop-wise addition of 5% NaOH solution. The fermentation experiments were carried out in 250 ml Erlenmeyer flasks, with a working volume of 100 ml. The flasks were closed with rubber stoppers vented with a syringe needle to release the $CO_2$ generated during fermentation. A nutrient solution containing $(NH_4)_2PO_4$, $NaH_2PO_4$, $MgSO_4.7H_2O$ and yeast extract was prepared. This solution was sterilized in the autoclave prior to use. Baker's yeast purchased from Sigma-Aldrich (St. Louis, Mo.) was dissolved in DI water at a concentration of 10 g DM/l and a 5 ml aliquot was added to each flask. The flasks were incubated at 30° C. in a rotating shaker set at 150 rpm and 1 ml samples were withdrawn at regular intervals. Samples were centrifuged at 4° C., 9000×g for 5 minutes and the supernatants stored frozen for analysis. Ethanol concentrations were measured using the Megazymes K-EtOH assay kit in which the concentration is calculated from the absorbance at 340 nm.

EXAMPLE 4

Enzymatic Hydrolysis and Fermentation of Example 2

Enzyme hydrolysis of the solid residue of Example 2 was performed as described above in Example 3 except that the solid residue of Example 2 was used instead of the solid residue of Example 1. Also, a surfactant TWEEN-80™(a polyethylene sorbitol ester, with a calculated molecular weight of 1,310 daltons, assuming 20 ethylene oxide units, 1 sorbitol, and 1 oleic acid as the primary fatty acid) was added to the enzyme hydrolysis medium. This is because binding of the lignin to the surfactant may prevent non-productive binding of enzymes to lignin and may improve cellulose hydrolysis

EXAMPLE 5

Theoretical Yield for Example 1 Above

In calculating the yield of example 1 above, if the ethanol/chlorine dioxide/water pretreatment successfully extracts all the cellulose and the enzymatic hydrolysis converts all of it to glucose, then 50.3 grams of glucose are obtained which can then result 25.65 g ethanol assuming 100 percent yield. After taking out the make-up ethanol for the process (3.3 g), the net ethanol yield would be 22.35 g. Advantageously, this compares well to the theoretical yield using a dilute acid pretreatment of Sweetgum, i.e., 50.3 g cellulose in starting material yields 36.68 g glucose in pretreated Sweetgum which yields 19.1 g glucose after enzymatic hydrolysis. This can then result in 8.75 g ethanol yield assuming 100 percent yield.
Conclusions Chlorine dioxide pretreatment appears to be more selective towards lignin than other potential pretreatments such as sulfuric acid. The resulting lignin has potential commercial applications. The residual solids resulting from chlorine dioxide treatments often have high glucose and low lignin content and therefore will often be amenable to enzymatic hydrolysis. The concentrations of sugar degradation products such as furans are often surprising and unexpectedly low in the effluents. This is advantageous since these degradation products can sometimes inhibit fermentation.

What is claimed is:

1. A process for treating a lignocellulosic feedstock, comprising:
    (a) contacting the lignocellulosic feedstock with a solution comprising chlorine dioxide, ethanol, and water to form a mixture;
    (b) heating the mixture at a temperature and time sufficient to produce a composition mixture comprising (1) a first solid portion comprising cellulose which is suitable for enzymatic hydrolysis, (2) a second solid portion comprising lignin, and (3) a solution comprising hemicellulose.

2. The process of claim 1, wherein the lignocellulosic feedstock has a holocellulose content of greater than 50 weight percent of the total feedstock as measured by NREL/TP 510-42618.

3. The process of claim 1, which further comprises enzymatically hydrolyzing at least part of the first solid portion to form a composition comprising glucose.

4. The process of claim 3, which further comprises fermenting the composition comprising glucose.

5. The process of claim 1, wherein the amount of chlorine dioxide employed in step (a) is from about 0.5% to about 8% by weight based on the total dry weight of feedstock employed.

6. The process of claim 1, wherein the feedstock is contacted with the solution comprising chlorine dioxide, ethanol, and water at a temperature of from about 50° C. to about 90° C. for a time of at least about 1 hour.

7. The process of claim 1, wherein the feedstock is contacted with the solution comprising chlorine dioxide, ethanol, and water at a temperature of from 60° C. to 80° C. for a time of at least about 2 hours.

8. The process of claim 1, wherein the mixture in step (b) is heated at a temperature of at least 180° C. for at least about 5 minutes.

9. The process of claim 1, wherein the mixture in step (b) is heated at a temperature of at least 180° C. for at least 30 minutes.

10. The process of claim 1, which further comprises separating the second solid portion comprising lignin from the solid first portion.

11. The process of claim 1, wherein the portions are separated by precipitating the second solid portion comprising lignin and recovering the lignin by filtration.

12. The process of claim 1, wherein the amount of ethanol is from about 40 to about 80 weight percent based on the total amount of ethanol and water.

13. The process of claim 1, wherein the ratio of feedstock to solution comprising chlorine dioxide, ethanol, and water is from about 1:3 to about 1:10.

14. The process of claim 1, wherein the conditions under which the feedstock is contacted with a solution comprising chlorine dioxide, ethanol, and water are sufficient to reduce the pH at least 1 unit prior to step (b).

15. The process of claim 1, wherein the lignocellulosic feedstock has an average particle size of less than about 25 mm in its smallest dimension.

16. The process of claim 1, wherein the lignocellulosic feedstock has an average particle size of less than about 10 mm in its smallest dimension.

17. A composition comprising a lignocellulosic feedstock and a solution comprising chlorine dioxide, ethanol, and water wherein the composition is characterized by (1) a ratio of feedstock to solution comprising chlorine dioxide and water of from about 1:3 to about 1:10; and (2) an amount of chlorine dioxide of from about 0.5% to about 5% by weight based on the total dry weight of dry feedstock.

18. The composition of claim 17, wherein the ethanol comprises from about 50 to about 70 percent by weight based on the total amount of ethanol and water.

19. The composition of claim 17, wherein the composition is characterized by (1) a ratio of feedstock to solution comprising chlorine dioxide and water of from about 1:3 to about 1:10; and (2) an amount of chlorine dioxide of from about 0.8% to about 1.5% by weight based on the total dry weight of dry feedstock.

20. A process for treating a lignocellulosic feedstock wherein the process comprises:
(a) contacting the feedstock with a solution comprising chlorine dioxide, ethanol, and water to form a mixture, wherein the ratio of feedstock to solution comprising chlorine dioxide, ethanol, and water is from about 1:3 to about 1:10, wherein the amount of ethanol is from about 40 to about 80 weight percent based on the total amount of ethanol and water, and wherein the amount of chlorine dioxide is from about 0.5% to about 8% by weight based on the total dry weight of feedstock;
(b) heating the mixture at a temperature of at least about 18° C. for at least about 5 minutes to produce a composition mixture comprising (1) a first solid portion comprising cellulose which is suitable for enzymatic hydrolysis, (2) a second solid portion comprising lignin, and (3) a solution comprising hemicellulose;
(c) separating the second solid portion comprising lignin from the solid first portion;
(d) enzymatically hydrolyzing at least part of the solid first portion to form a composition comprising glucose; and
(e) fermenting the composition comprising glucose.

* * * * *